United States Patent [19]
Asai et al.

[11] Patent Number: 5,715,182
[45] Date of Patent: Feb. 3, 1998

[54] DEVICE FOR THE CLASSIFICATION AND EXAMINATION OF PARTICLES IN FLUID

[75] Inventors: Hideki Asai, Mito; Hideyuki Horiuchi, Abiko; Ryohei Yabe; Norio Oowada, both of Katsuta, all of Japan

[73] Assignee: Hitachi, Ltd., Tokyo, Japan

[21] Appl. No.: 286,257

[22] Filed: Aug. 8, 1994

[30] Foreign Application Priority Data

Aug. 19, 1993 [JP] Japan .................................. 5-204834
Oct. 15, 1993 [JP] Japan .................................. 5-258049

[51] Int. Cl.$^6$ .................................................. G06F 19/00
[52] U.S. Cl. ................... 364/555; 364/413.11; 395/924; 356/441
[58] Field of Search ................ 364/413.07, 413.08, 364/413.09, 413.1, 413.11, 413.13, 496, 497, 499, 555, 413.01; 356/39, 40; 395/21, 924, 902

[56] References Cited

U.S. PATENT DOCUMENTS

| | | |
|---|---|---|
| 4,338,024 | 7/1982 | Bolz et al. |
| 4,393,466 | 7/1983 | Deindoerfer et al. ................ 364/497 |
| 4,404,683 | 9/1983 | Kobayashi et al. ................ 382/6 |
| 4,612,614 | 9/1986 | Deindoerfer et al. ................ 364/497 |
| 4,965,725 | 10/1990 | Rutenberg ................ 364/413.1 |
| 5,257,182 | 10/1993 | Luck et al. ................ 364/413.1 |
| 5,287,272 | 2/1994 | Rutenberg et al. ................ 364/413.01 |

FOREIGN PATENT DOCUMENTS

| | | |
|---|---|---|
| 361504 | 4/1990 | European Pat. Off. . |
| 466168 | 1/1992 | European Pat. Off. . |
| 501005 | 9/1992 | European Pat. Off. . |
| 515100 | 11/1992 | European Pat. Off. . |
| 543414 | 5/1993 | European Pat. Off. . |
| 551010 | 7/1993 | European Pat. Off. . |
| 556971 | 8/1993 | European Pat. Off. . |
| 0575091 | 12/1993 | European Pat. Off. . |
| 4404896 | 8/1994 | Germany . |
| 60-38653 | 2/1985 | Japan . |
| 3-100876 | 4/1991 | Japan . |
| 3-41783 | 6/1991 | Japan . |
| 3-52573 | 8/1991 | Japan . |

*Primary Examiner*—Emanuel T. Voeltz
*Assistant Examiner*—M. Kemper
*Attorney, Agent, or Firm*—Fay, Sharpe, Beall, Fagan, Minnich & McKee

[57] ABSTRACT

A particle image in a sample is formed at an imaging position by an objective lens of a microscope, projected on the image picking up plane of a TV camera via a projection lens and is subjected to photo-electric conversion. Image signals from the TV camera are supplied to an image memory via an A/D converter as well as to an image processing control unit. Image signals outputted from the image memory are supplied to a characteristic picking out unit and there a plurality of characteristics of the particle concerned are picked out. The picked-out characteristics are supplied to the classification unit and there classification of the sediment components is perfumed via a neural network with a learning capability. Accordingly, the classification unit performs provisionally an automatic classification of the objective sediment components by making use of the inputted characteristic parameters.

The device allows accurate and fast automatic component particle analysis even for patient specimens containing a variety of components in high concentration.

14 Claims, 14 Drawing Sheets

FIG. 3

| | |
|---|---|
| LEUCOCYTE | LEUCOCYTE |
| EPITHELIAL CELL | GRANULAR CAST |

ID   : 0001
NAME : HITACHI TARO
SEX  : MALE

TEST DATE
93. 03. 03   11:15

[ CONTINUE ]   [ END ]

PAGE 1

FIG. 4

EPITHELIAL CELL

ID   : 0001
NAME : HITACHI TARO
SEX  : MALE

TEST DATE
93. 03. 03   11:15

[ CONTINUE ]   [ END ]

PAGE 1

MENU  ENTIRE DELETION  CONTINUE TO SUBSEQUENT PAGE  PREVIOUS PAGE  END

MODE: HIGHLY ENLARGED
SCALE ⊢—⊣ 20μm
PARTICLE NUMBER
HPF: 12345  LPF: 67890

PATIENT SPECIMEN NO. : 1
ID : 0123456789012
DATE : 93/ 1/28
TIME : 12:20

DISPLAY ITEM: FLAT EPITHELIAL

| | | | | |
|---|---|---|---|---|
| LEUCOCYTE | : 5 | ERYTHROCYTE | : 10 | FLAT EPITHELIAL : 11 | MIGRATING EPITHELIAL : 0 | RENAL TUBULE EPITHELIAL : 0 |
| SMALL CIRCULAR EPITHELIAL | : 0 | HETEROMORPHIC CELL : 0 | GLASSY CAST : 0 | WAXLIKE CAST : 0 | LEUCOCYTE CAST : 0 |
| ERYTHROCYTE CAST | : 0 | EPITHELIAL CAST : 0 | GRANULAR CAST : 0 | FUNGUS : 0 | YEAST : 0 |
| URATE | : 0 | OXALATE : 0 | TYROSINE : 0 | LEUCINE : 0 | MUCOUS THREAD : 5 |
| UNIDENTIFIABLE | : 3 | DUST : 40 | | | |

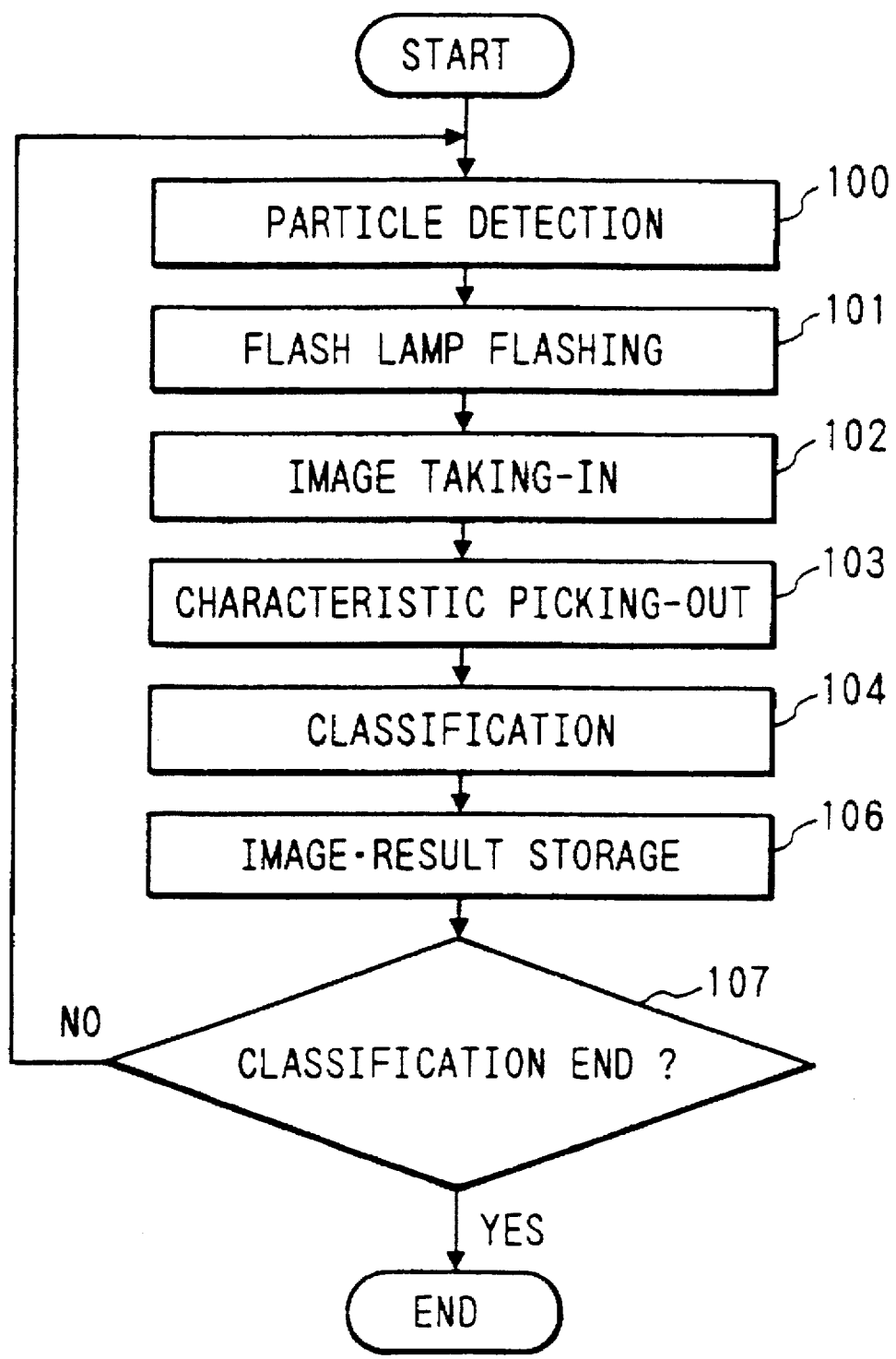

DEVICE FOR THE CLASSIFICATION AND EXAMINATION OF PARTICLES IN FLUID

BACKGROUND OF THE INVENTION

The present invention relates to device for the classification and examination of particles in fluid and, in particular, relates to a classification and examination device which is suitable for use in the automatic classification and examination of sediments in urine and of blood corpuscles in blood.

When an examination engineer performs a visual examination on particles in fluid, for example, on sediment components in urine, the urine which is the object for the examination is centrifuged and precipitated sediments are dripped onto a slide glass. Then, if necessary, after coloring the sediments on the slide glass, a specimen is prepared and the examination engineer visually observes the specimen through a microscope.

Other than the above conventional method in which an examination engineer performs a visual examination on the sediment components in urine, devices which automate these examinations are proposed in which particles are flowed in a flow cell while being suspended in liquid and optically analyzed.

For example, JP-B-3-52573(1991), which corresponds to U. S. Pat. No. 4,338,024, discloses a particle analysis device in which a fluid specimen is passed through a fluid passage having a specific configuration so as to confine particles in the specimen in an extended image taking area and to produce still images thereof. With this particle analysis device a shape analysis of the particles is possible through an image analysis of the still images which allows an automatic classification of sediments in urine with regard to the sediment shape.

JP-B-3-41783(1991) discloses a conventional particle classification and display device in which, after taking in images of particles in fluid, a predetermined image processing is performed thereon, and in such image processing only the particle portions are cut out from the entire image for display purposes such that the particles could not be identified automatically with the image processing.

Further, JP-A-3-100876(1991) discloses a device having a further advanced image processing function in which edge detection of particle images and cutting out of the particle image portions from the entire image are performed. However identification of the particles still must be performed manually.

Still further, JP-A-60-38653(1985), which corresponds to U. S. Pat. Nos. 4,393,466 and 4,612,614, discloses a particle analysis method for a fluid specimen in which images of particles are displayed in a predetermined order. With this particle analyzing method, the images of the particles are displayed in an ordered array by classes of visually discernible characteristics and thus the particle images are displayed in an order of size and color thereof. The method of JP-A-60-38653(1985) requires a user operator to examine and confirm the displayed screen image, and no automatic classification function is included. Thus, the particles are grouped according to particular parameters, such as size of the particles, and are displayed, which is however insufficient even as a supplementing function for further detailed reclassification afterward by the user operator.

In the method disclosed in JP-B-3-52573(1991), the storage of the images and display thereof with regard to urine of healthy persons are performed comparatively easily, because the sediment components in the urine are extremely limited. However, in contrast to the urine of healthy persons, the urine of non-healthy persons contains a variety of sediment components such as non-crystalline salts, mucous threads, erythrocytes and leucocytes in high concentration and characteristics of these component particles, for example ranges of their shapes and sizes, overlap each other. The method disclosed in JP-B-3-52573(1991) is sufficient for screening the urine of non-healthy persons from urine of healthy persons, but an accurate analysis on specimens containing a variety of component particles such as non-crystalline salts, mucous threads, erythrocytes and leucocytes in high concentration cannot be realized.

Further, when a specimen containing a variety of components in high concentration is analyzed by making use of the method disclosed in JP-A-60-38653(1985), the component particles are displayed in an order such as size and color, and therefore particles belonging to different types are displayed at the same time. For example, when the component particles are displayed in an order of size, leucocytes and erythrocytes are displayed on a screen at the same time in a mixed manner, because the size ranges of leucocytes and erythrocytes overlap each other. Further, when the component particles are displayed in an order of color, glassy casts and mucous threads are displayed on the screen at the same time in a mixed manner, because the colors of glassy casts and mucous threads are similar to each other.

Moreover, in the method disclosed in JP-A-60-38653 (1985), images of all of the detailed particles are displayed on the screen. For this reason, as the urine of non-healthy persons contains a great many sediment components as explained above, it takes a long time for displaying all of the particle images and for judging the respective displayed particle images, and it is possible to miss sediment components (for example, heteromorphic cells and cancer cells) which appear infrequently but have a significant implication for diagnosis. Still further, it is required to have memory capacity to store all of the images of the appeared sediments such that it is quite difficult to store data of many specimens at the same time.

In the conventional particle classification device, even though a classification of particles such as according to particle size can be displayed, classification of the particles with regard to types and characteristics has to be performed by a user operator over all particles, which requires significant man-hours, and which is problematic.

As explained above, with the conventional methods it has been difficult to perform an accurate and fast urine sediment analysis on specimens containing a variety of components in high concentration.

SUMMARY OF THE INVENTION

An object of the present invention is to resolve the conventional problem and to provide a particle classification and examination device which detects characteristic parameters of the respective particles such as area, circumferential length, maximum X axis coordinate, minimum X axis coordinate, maximum Y axis coordinate, minimum Y axis coordinate, X axis projection length, Y axis projection length, red color concentration, green color concentration and blue color concentration, and automatically determines the types of the respective particles to thereby eliminate man-hours for the particle classification, stores and displays the classification results and the particle images altogether and permits alternation of the characteristic parameters, preparation of learning data and relearning to thereby improve the time-to-time classification accuracy.

Another object of the present invention is to realize a device for the classification and examination of particles in fluid which can automatically perform an accurate and fast component particle analysis even for a specimen containing a variety of components in high concentration.

For achieving the above objects of the present invention, the particle classification and examination device according to the present invention is constituted by an image picking up unit which picks up images of respective particles dispersed in a specimen flowing in a fine tube, and an image processing unit which analyzes the picked up particle images, classifies the particles and displays the same, wherein the image picking up unit picks up colored images of the respective particles; and the image processing unit converts each of the colored particle images into at least one binary image signal based on a color standard, calculates a characteristic quantity of the respective particles based on the binary image signal, automatically classifies the respective particles based on the characteristic quantity and displays the colored particle images according to the classification result.

Further, the image processing unit is constituted to include a function which stores the colored particle images and the automatic classification results, and another function which correlates the colored particle images and the automatic classification results and stores the same.

Still further, the image processing unit comprises a function which stores either the colored particle images or the automatic classification results together with related data with the specimen inputted by a user operator such as name of patient, ID number of the patient, medical examination department, examination data, name of doctor, other examination results such as urine qualitative analysis, blood test, patient's condition and specimen condition such as turbidity, color, amount.

Still further, the image processing unit comprises a function which stores both the colored particle images and the automatic classification results together with the related data with the specimen inputted by a user operator.

Still further, the image processing unit comprises a function which arranges at least one colored particle image in a predetermined order of classification types according to the automatic classification results and displays the same on a screen at the same time.

Still further, the image processing unit comprises a function which displays the colored particle images and the automatic classification results on a screen at the same time while correlating the two with each other.

Still further, the device comprises means for permitting reclassification and learning based on the display of the colored particle images and provisional automatic classification results.

Further, for achieving the above objects of the present invention, the classification and examination device, which detects particles in fluid and picks up images of the detected particles, is constituted by: a characteristic picking out unit which picks out a plurality of characteristics from the detected particles; a type identifying unit which identifies types of particles based on a plurality of the picked out characteristics of the particles; a storage unit which stores at least an image of a particle of which the type identifying unit fails to identify the type thereof; and a display unit which displays the image stored in the storage unit.

Further, the classification and examination device of particles in fluid, which detects particles in fluid and picks up images of the detected particles, is constituted by: a characteristic picking out unit which picks out a plurality of characteristics from the detected particles; a type identifying unit which identifies types of particles based on a plurality of the picked out characteristics of the particles; a storage unit which stores the picked up particle images and the identified types of the particles by the type identifying unit; and a display unit which selectively displays the images stored in the storage unit.

Further preferably, in the classification and examination device of particles in fluid, the type identifying unit identifies types of the particles based on a neural network logic having a self learning capacity.

According to the constitution of the present invention, the image processing unit takes in colored images of the particles, breaks down the colored particle images depending on colors, generates at least one binary coded image, determines characteristic parameters such as area and average concentration corresponding to the particle portions in the binary coded image, and automatically identifies the respective particles based on their characteristic parameters so that conventionally required man-hours as well as waiting necessity of a user operator's judgment input are avoided.

Further, since the particle images, the classification results and the related data with the specimen are altogether stored and displayed, the properness of the classification results is very understandable at the time when analyzing the classification results in detail.

Still further, when a neurocomputer is used for the classification logic in the particle classification and examination device, an alternation of the characteristic parameters for the neuro calculation can be easily achieved, as well as the preparation of learning data and relearning can be performed only within the particle classification and examination device, which improves the classification accuracy at every operation time thereof.

A plurality of characteristics of respective particles picked out in the characteristic picking out unit are fed to the type identifying unit. The type identifying unit estimatedly determines types of the particles based on a plurality of the fed characteristics. With regard to particles of which type cannot be estimatedly determined by the type identifying unit, the images thereof are stored in the storage unit. Then, the stored images are displayed by the display unit and the displayed contents are examined by a user such as an examination engineer, and the types of the particles are determined by the user.

BRIEF DESCRIPTION OF THE DRAWINGS

FIG. 3 is an explanatory view of a displayed screen image in the particle classification device of the embodiment as shown in FIG. 1;

FIG. 4 is an explanatory view of another displayed screen image in the particle classification device of the embodiment as shown in FIG. 1;

FIG. 6 is an explanatory view of a displayed screen image of a subclassification of an automatic classification result in the particle classification device of the embodiment as shown in FIG. 1;

FIG. 12 is a view illustrating an example of displayed screen images;

FIG. 13 is an operation flowchart of a further embodiment according to the present invention;

DETAILED DESCRIPTION OF PREFERRED EMBODIMENTS

Figure 1:
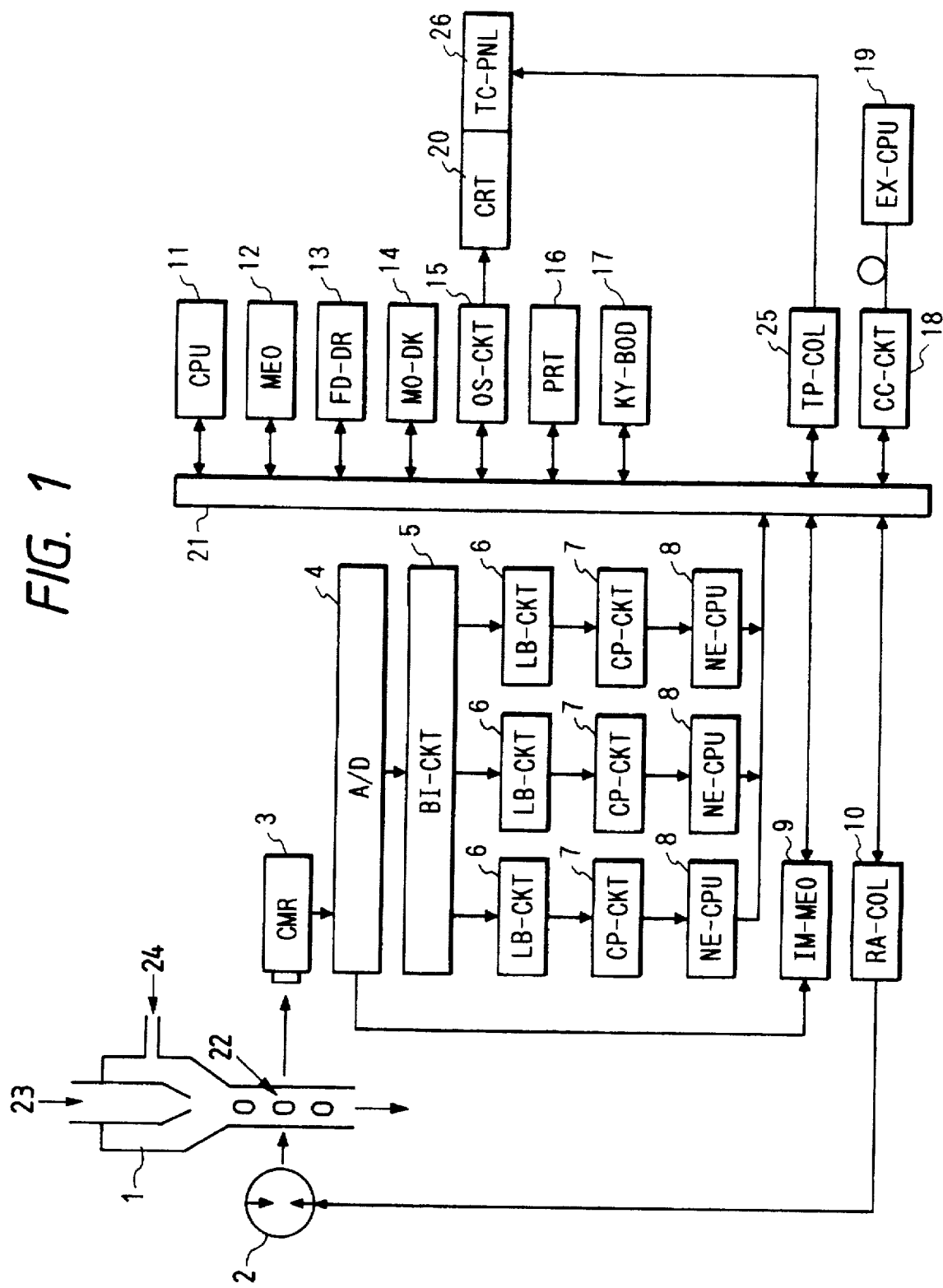
FIG. 1 is a block diagram illustrating a constitution of a particle classification device of one embodiment according to the present invention.

Hereinbelow, an embodiment according to the present invention is explained with reference to FIG. 1 through FIG. 8.

The particle classification device of one embodiment according to the present invention which is applied for classifying sediment components in urine is explained with reference to FIG. 1.

A urine sample 23 containing sediment component particles in urine to be examined flows down in a flow cell 1 while being surrounded by a sheath flow 24.

The sample urine 23 and the sheath flow 24 are fed into the flow cell 1 by a fluid pump (not shown), the control of which is performed by a CPU 11.

Sediment component particles 22 in the sample urine 23 are controlled to flow through the flow cell 1 substantially at the center of the flowing down fluid by the sheath flow 24.

The sediment component particles 22 in urine in the flow cell 1 are illuminated by a pulse-like flash of light from a flash lamp 2 and then converted into electrical image signals via a CCD camera 3.

The converted colored particle image signals are further converted into digital signals via an A/D converter 4. The digital signals are sent to a binarizing circuit 5 and at the same time sent to an image memory 9 where the digital signals are stored.

The binarizing circuit 5 discriminates the inputted digital image signals according to their color standard and converts them into a plurality of binary image signals. Since there can exist a plurality of sediment component particle images in the binary image signals, the sediment component images are then subjected to a so called labelling operation; in other words, corresponding numbers are assigned thereto via a subsequent labelling circuit 6.

From the respective labelled sediment component images characteristic quantities such as area, circumferential length and average concentrations of respective red, green and blue colors of every sediment component image are picked out via a characteristic picking out circuit 7.

The picked out characteristic quantities of the respective particles are inputted into a particle classification and identification circuit 8 and the respective sediment components are classified and identified.

The binarizing circuit 5, the labelling circuit 6, the characteristic picking out circuit 7, and the particle classification and identification circuit 8 are provided respectively in three sets for covering respective colors of red, green and blue, and are controlled by the CPU 11 to which elements such as a memory 12, a floppy disk drive 13, a magneto-optic disk 14, an image display circuit 15, a printer 16 and a key board 17 are connected via a CPU bus 21. To the image display circuit 15 is connected an image display CRT 20 to which a touch panel 26 is attached.

The touch panel 26 is designed to allow inputs by a user operator in an interactive manner with the CRT 20 through a touch panel control circuit 25.

Further, the CPU 11 is also designed to allow telecommunication with an external computer 19 via a telecommunication circuit 18 such that results such as classification and an abnormality of the present device can be communicated to the external computer 19.

In the present embodiment, an example of using a neurocomputer for the particle identification is explained. FIG. 2 shows a neurocomputer network for particle identification used in the particle classification device of the embodiment in FIG. 1.

The neurocomputer used in the present embodiment is a Rumelhart type having a three layer structure.

The inputs for the neurocomputer are characteristic parameters such as area and circumferential length of the particle images, and the outputs thereof are types of the particles such as erythrocyte, leucocyte, epithelial cell, cast and microbe. Through increasing the node number in the network, further finer classification can be realized, for example the casts can be subclassified into such as glassy cast, granular cast, erythrocyte cast and epithelial cast. An output having the maximum value among the output values from the neurocomputer is determined as the classification result.

The classification result and the colored particle image digital signals stored in the image memory 9 are recorded on the magneto-optic disk 14 as a single file.

Since the neurocomputer is used for classification and learning with respect to the particles, output values for the respective classification items or types are in addition filed. At the same time, the results are displayed on the CRT in addition to the colored particle images. Such display can be performed for every particle according to the measurement order or alternatively can be performed collectively after completing classification for one patient specimen.

Figure 2:
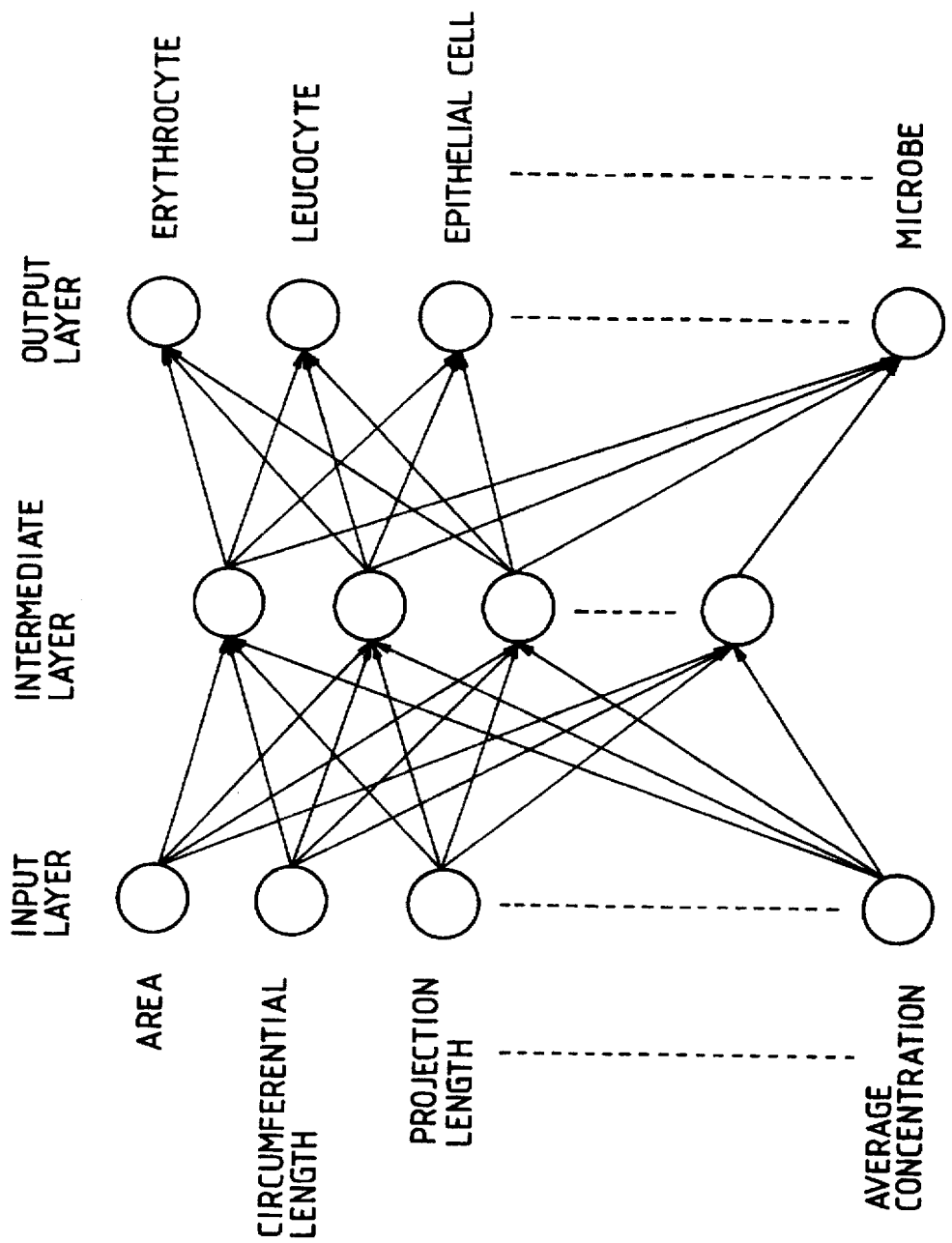
FIG. 2 is a network diagram of a neurocomputer used in the particle classification device of the embodiment as shown in FIG. 1.

Further, FIG. 3 is a displayed screen image of the particle classification device of the embodiment as shown in FIG. 1, displaying at the same time particle images and the automatic classification results thereof. In the respective frames in the drawing the particle images and the corresponding automatic classification results are displayed at one-to-one correspondence.

FIG. 4 is a displayed screen image of the particle classification device of the embodiment as shown in FIG. 1 displaying particle images classified for the same classification item.

These results can be outputted through the printer 16 and at the same time can be transferred to the external computer 19 via the telecommunication circuit 18.

The above series of operations for the particle image automatic classification is controlled by the CPU, 11, the control program which is inputted via a floppy; and disk and is executed after loading the same into a memory. Further, the manipulation thereof is performed via an input from the key board 17.

Still further, if the touch panel 26 is provided in the present embodiment, the inputting can be performed via the touch panel 26.

For example, when a further subclassification is required, or when a correction of the automatic classification results is required, a user operator can subclassify or correct the automatic classification results while examining the images after the automatic and provisional classification is completed.

Figure 5:
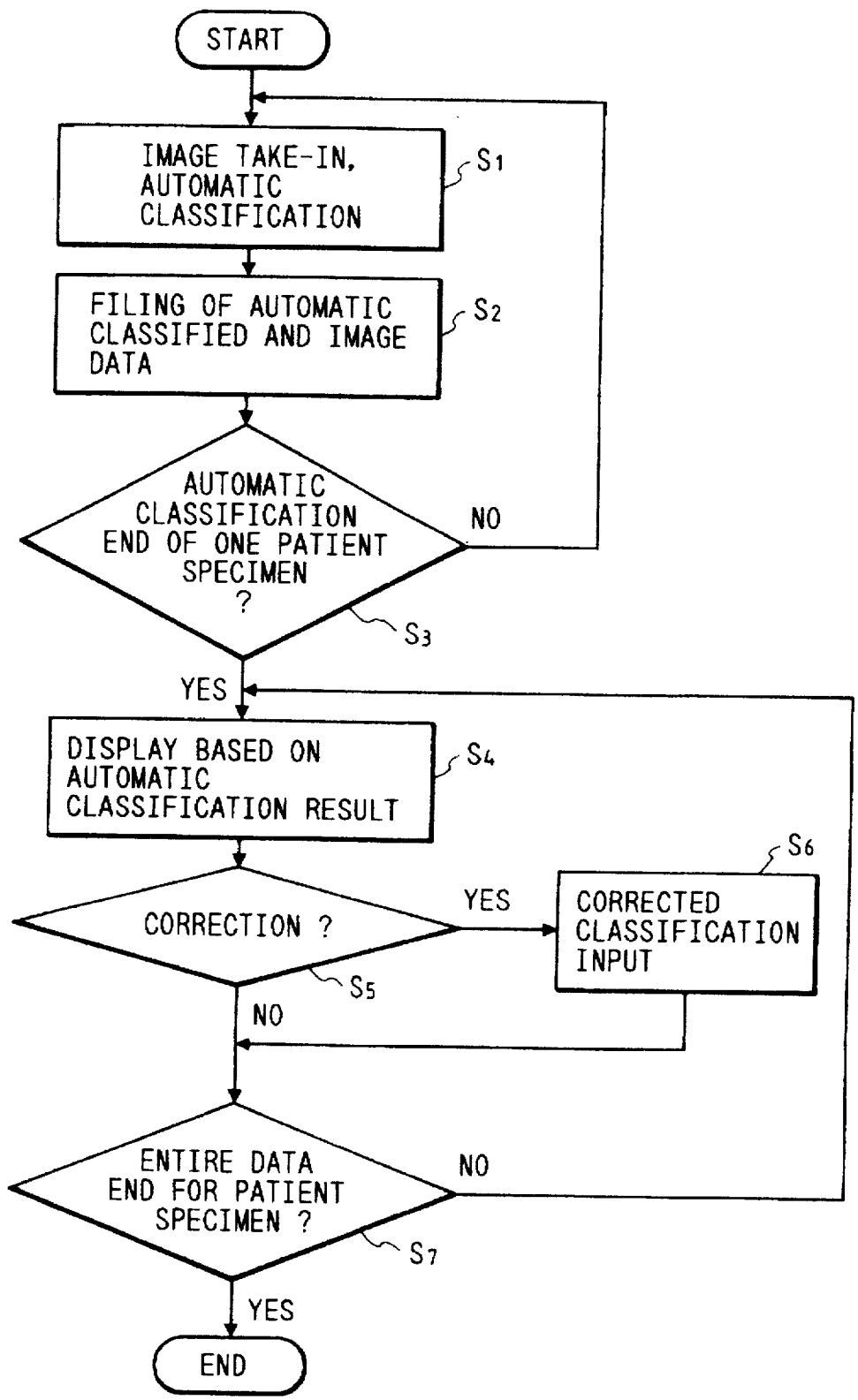
FIG. 5 is a flowchart illustrating a correction sequence of an automatic classification result in the particle classification device of the embodiment as shown in FIG. 1.

The correction sequence of the automatic classification results in the particle classification device of the embodiment as shown in FIG. 1 is explained with reference to the flowchart as shown in FIG. 5.

The following is, an example, wherein entire classification data are taken in for every patient specimen. Thereafter the automatic classification results are collectively displayed for every classification item and then a user operator inputs subclassification and correction data via the touch panel 26.

Step S1 through step S7 show the respective sequences. In step S1 through step S3 particle images of the respective particles of one patient specimen are taken in and the automatic classification is performed thereon.

In step S1, one particle image of the patient specimen is taken in via the CCD camera 3, the binarized characteristics are picked out therefrom, and the automatic classification is performed thereon via the neurocomputer 8.

Subsequently, in step S2 the classification results and the image data obtained at step S1 are stored in the magneto optic disk 14 and filed.

In step S3, a checking whether all of the data collection for the patient specimen is completed, and if not completed, the process returns to step S1. If completed, the process advances to the subsequent step S4.

Step S4 through step S7 show sequences wherein the user operator performs subclassification or the correction on the results obtained during the automatic classification.

In step S4, the colored particle image data associated with the automatic classification results stored in the magneto optic disk are displayed on the CRT display 20 for every classification item.

In the subsequent step S5, the user operator checks whether the automatic classification results are to be corrected based on the displayed particle images. If it is determined that a correction thereof is necessary, the user operator causes the process to move to step S6, and if it is determined that a correction thereof is unnecessary, the user operator causes the process to move to step S7. When the user operator inputs an input indicative of correction necessity in step S5, the user operator inputs a correction data which is determined by himself in the subsequent step S6 and then causes the process to move to step S7.

In step S7, a checking is performed to determine whether reviewing of all of the data is completed. When the user operator reviews all of the data and completes necessary corrections, it is determined that the process for one patient specimen has been completed, and then the process goes END.

When correction for all of the data has not been completed, the process returns again to step S4, and step S5 through S7 are repeated.

Figure 6:
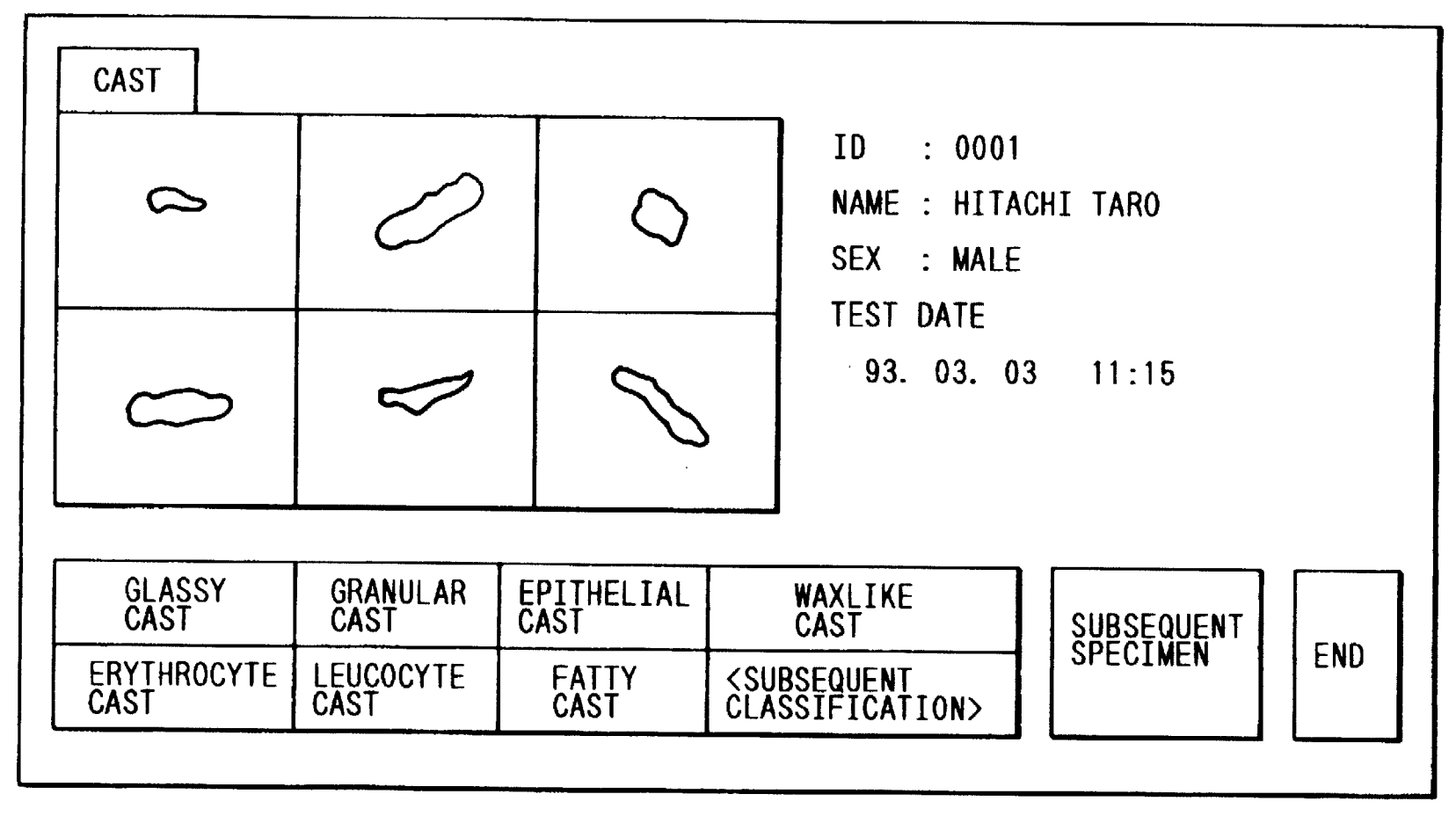

A subclassification of the automatic classification results in the particle classification device of the embodiment as shown in FIG. 1 is explained with reference to FIG. 6. In the present example, sediment components classified as casts via the automatic classification unit are collectively displayed and these casts are classified and identified, for example, as glassy cast and granular cast.

The input operation for the above subclassification is performed in the following manner. At first, an image on the screen of which classification is desired is touched. Through this touching an image selection signal is inputted in the touch panel 26 and the image is selected.

Then, a classification item at the bottom of the screen is determined by the user operator viewing the selected image and is touched. Thereby, a subclassification is determined and inputted. The above operation is performed for all of the necessary images.

When images to be classified are exhausted, one of "subsequent specimen" or "end" on the screen is touched. Through these sequences the subclassification and the correction are performed.

Figure 7:
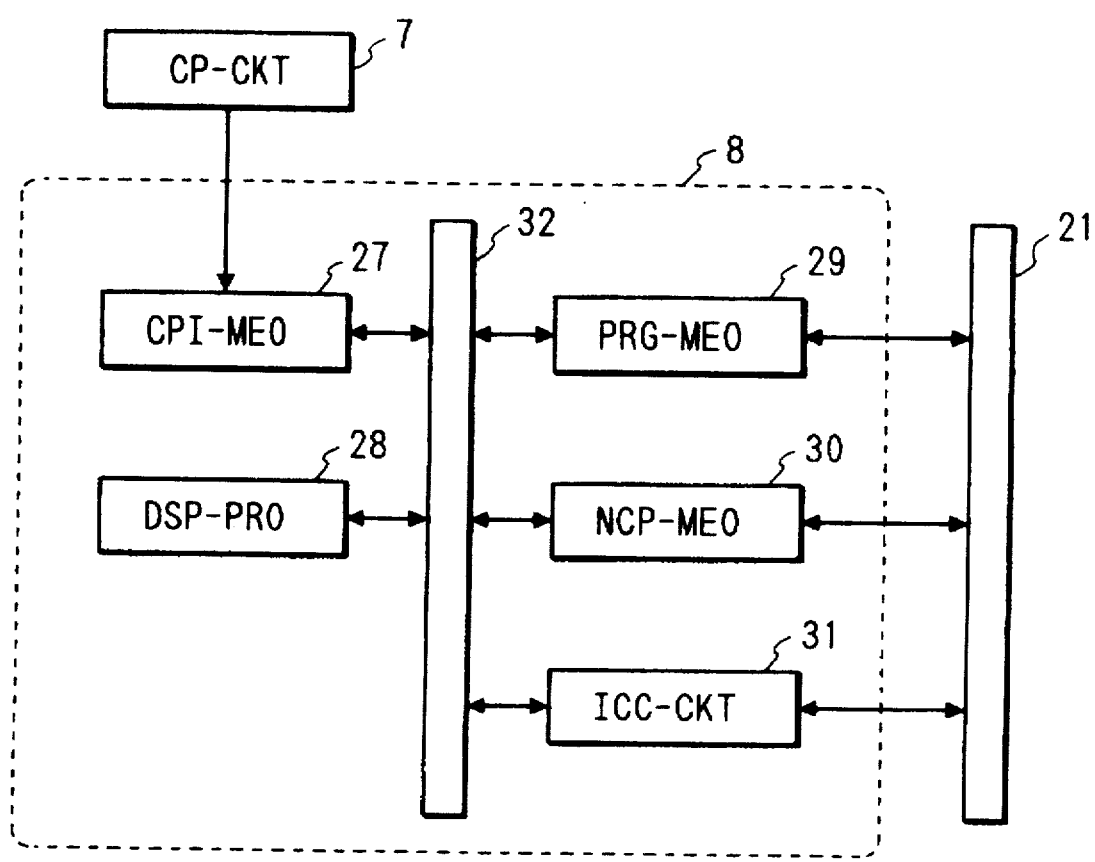
FIG. 7 is a block diagram of a neurocomputer used in the particle classification device of the embodiment as shown in FIG. 1.

Now, the neurocomputer for identification used in the present embodiment is explained. FIG. 7 shows a block diagram when a neurocomputer is used for the particle identification unit 8 in the particle classification device of the embodiment as shown in FIG. 1, in which the elements bearing the same reference numerals as in FIG. 1 designate the same or equivalent elements as in FIG. 1 and the explanation thereof is omitted.

In FIG. 7, the neurocomputer 8 is constituted by such as a characteristic parameter input memory 27, a digital signal processing processor 28, a program memory 29, a neuro calculation parameter memory 30 and an inter CPU telecommunication circuit 31 which are connected with each other via a digital signal processing processor bus 32.

In like manner, the program memory 29, the neuro calculation parameter memory 30 and the inter CPU telecommunication circuit 31 are connected to the CPU 11 (not shown in FIG. 7) via the CPU bus 21.

A neuro calculation is performed in the digital signal processing processor 28. The programs for the neuro calculation are loaded into the program memory 29 from the CPU 11 via the CPU bus 21, and parameters for the neuro calculation are loaded into the neuro calculation parameter memory 30 from the CPU 11 via the CPU bus 21.

The characteristic parameters necessary for the above calculation are provided from the characteristic picking-out circuit 7 via the characteristic parameter input memory 27 and the calculation results are transferred to the inter CPU telecommunication circuit 31.

The values at the output layer in the network of the neurocomputer as shown in FIG. 2 are transmitted to the CPU 11, and at the same time a particle identification result determined based on the output exhibiting the maximum value is also transmitted.

In the present embodiment, the parameters for the neuro calculation are designed to be rewritable, and the classification logic can be altered by rewriting the neuro calculation parameters stored in the floppy disk.

Now, a neuro learning in the particle classification device of the present embodiment is explained. For the first time, measurement of sample urine is performed in the same manner as in the classification explained above. Then, a user operator reclassifies the result, adds the reclassified results into learning data which have been accumulated from the past as additional learning data and renews the learning data.

Figure 8:
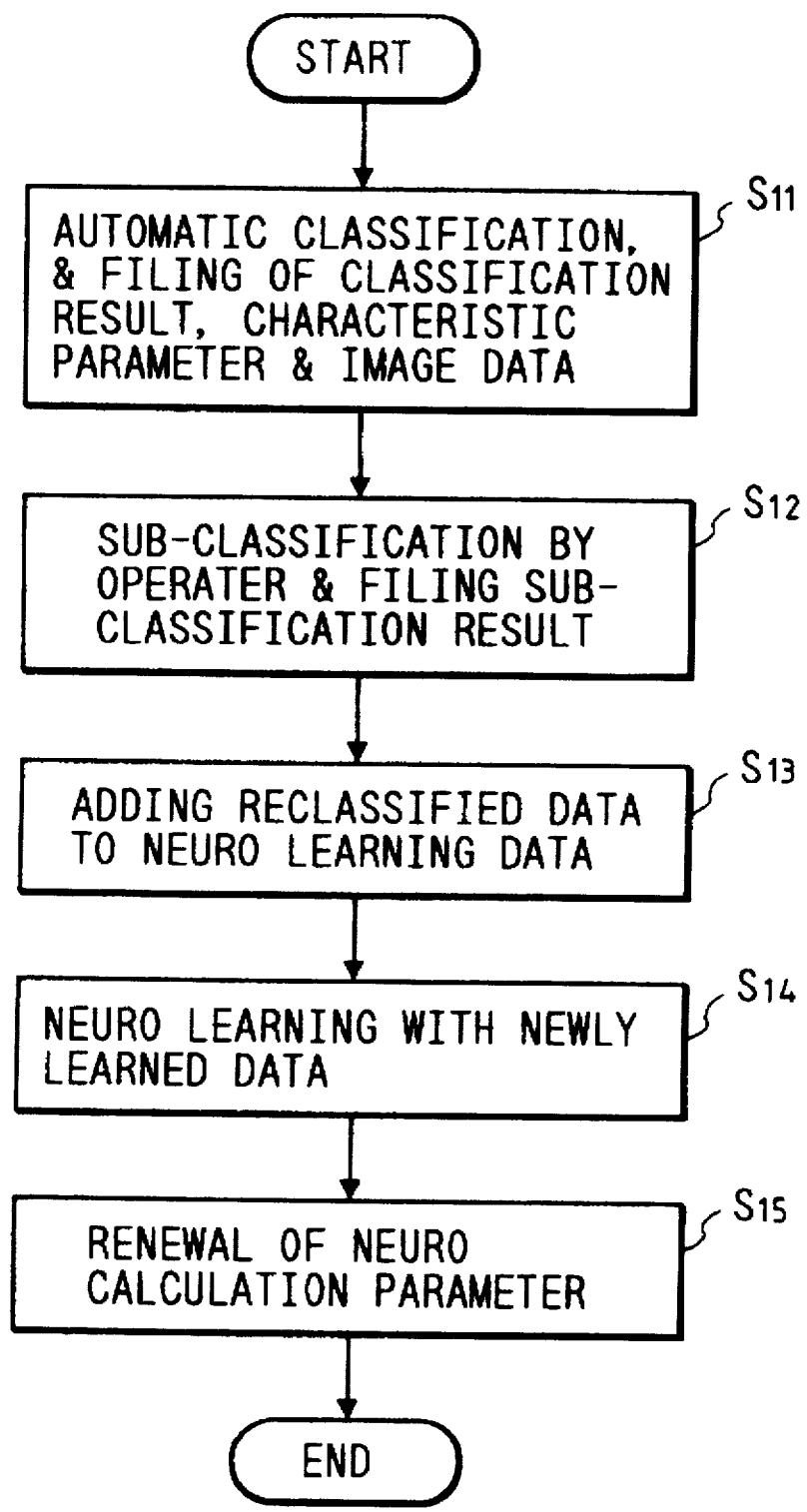
FIG. 8 is a flowchart illustrating a learning sequence of the neurocomputer in the particle classification device of the embodiment as shown in FIG. 1.

FIG. 8 is a flowchart illustrating a learning sequence of the neurocomputer in the particle classification device of the embodiment as shown in FIG. 1.

Step S11 through step S15 show the above learning sequence. At first, in step S11, a data collection and an automatic classification for one patient specimen and filing of the classification results and image data are performed.

The sequence in step S11 is identical to that in step S1 through step S3 relating to the correction sequence of the automatic classification results as explained in connection with FIG. 5, and further the sequence in step S12 is identical to that in step S4 through step S7 as explained in connection with FIG. 5. Thus, the detailed explanation thereof is omitted for avoiding duplication and complexity.

In step S13, the classification result corrected by the user operator at step S12 is added to the neuro learning data contained in the particle classification device itself to make a teacher data for the learning and to form a new neuro learning data.

In step S14, a learning of the neurocomputer is performed based on the new neuro learning data by making use of a so called back propagation method.

In step S15, calculation parameters such as the neurocomputer weighting parameter obtained in the learning at step S14 can be rewritten and renewed.

Through the sequences as explained above, a relearning of the neurocomputer is performed and the amount of the accumulated data is increased through which an improvement of classification accuracy is greatly expected.

In the present embodiment, classification of sediment components in urine is explained. However, with the particle classification device according to the present embodiment a corpuscle classification can likely be performed by modifying the binarized threshold values and the neuro calculation parameters suitable for the corpuscle classification in blood.

According to the present embodiment, as explained in detail in the above, a particle classification and examination device is provided which picks out characteristic parameters of the respective particles and automatically and provisionally determines the classification of the respective particles to thereby eliminate man-hours for the particle classification, stores and displays the classification results and the particle images altogether and permits alternation of the characteristic parameters and preparation of learning data and relearning to thereby improve the time-to-time classification accuracy.

Hereinbelow, further embodiments of the present invention are explained with reference to FIG. 9 through FIG. 15.

Figure 9:
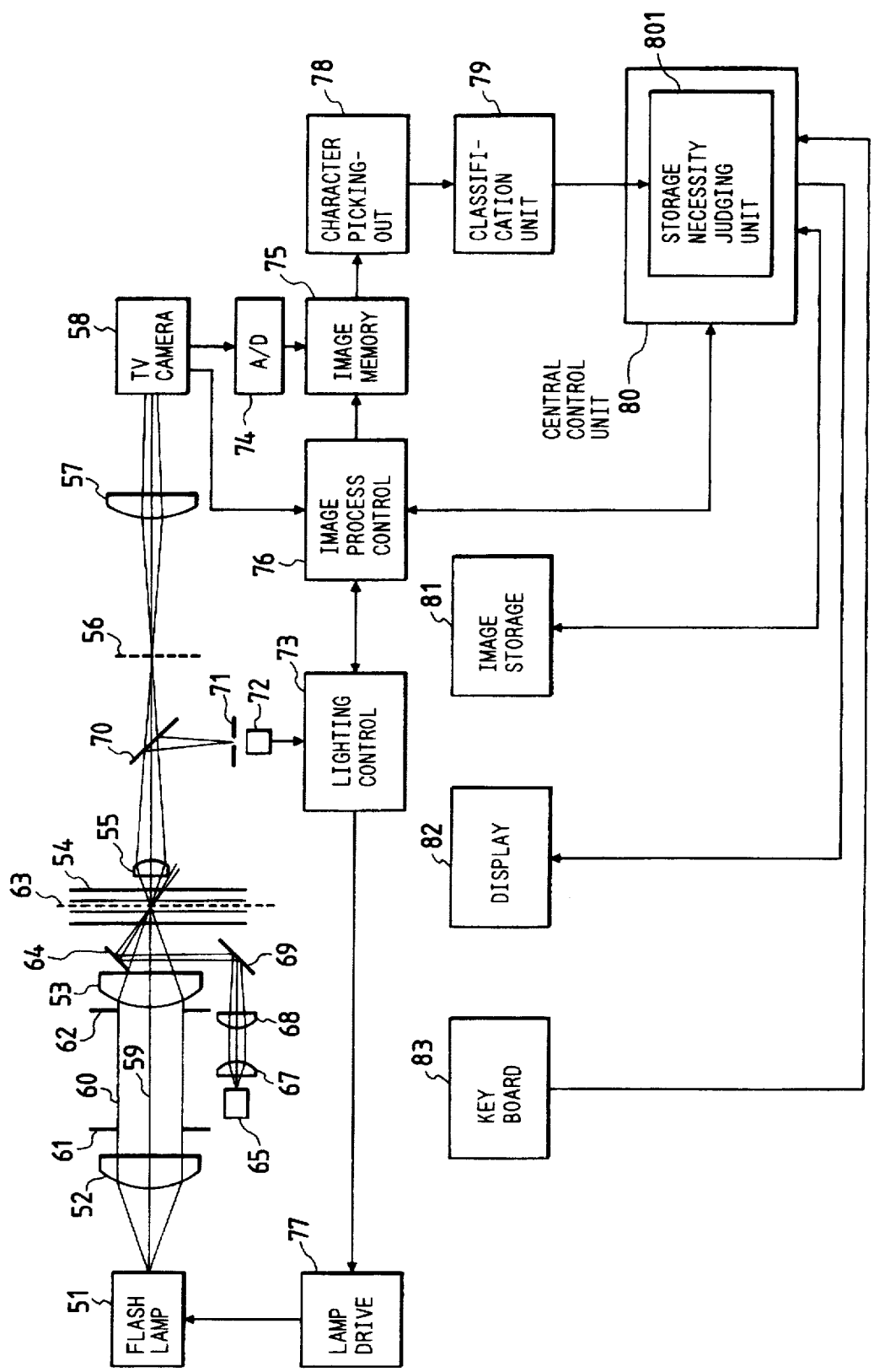
FIG. 9 is a schematic constitutional diagram of another embodiment according to the present invention.

FIG. 9 is a schematic constitutional diagram of another embodiment of the device for the classification and examination of particles in fluid according to the present invention which is applied to a classification and examination device for urine sediments.

In FIG. 9, light generated from a flash lamp 51 constituting a light source for a microscope advances along an optic axis of the microscope, passes through a field lens 52, is restricted by a field stop 61 and an aperture stop 62 and forms a light source flux 60. Then the light flux 60 is condensed via a condensor lens 53 onto a sample 63 flowing within a flow cell 54.

A particle image of the sample 63 is formed at an imaging position 56 by an objective lens 55 of the microscope. The particle image at the imaging position 56 is projected on the image picking up plane of a TV camera 58 via a projection lens 57 and subjected here to photo-electric conversion. For the TV camera 58, for example, a CCD (Charge Coupled Device) type TV camera having a limited after image is used. Further, since the diameter of objects for the urine sediment examination varies from less than 1 μm to 200 μm which requires a broad measurement range, the projection magnification of the TV camera 58 is designed to be switched by the projection lens 57 depending on necessity.

Image signals from the TV camera 58 are supplied to an image memory 75 via an A/D converter 74 as well as to an image processing control unit 76. The image processing control unit 76 executes controls of processes such as image writing and image processing for the image memory 75.

Image signals outputted from the image memory 75 are supplied to a characteristic picking out unit 78 and there a plurality of characteristics of the particles concerned are picked out. Namely, via the characteristic picking out unit 78 primary parameters of the sediment components such as shape, color and size are picked out. The characteristic picking out unit 78 supplies to a classification unit or an identification unit 79 the primary parameters and secondary parameters which are generated through combined calculations of the primary parameters.

The classification unit 79 uses a Rumelhart type neural network and performs classification of the sediment components. The neural network has performed in advance learning by making use of a great many data checked by experts, and coupling coefficients between respective neurons are optimized. Accordingly, the classification unit 79 performs a neural network calculation by making use of inputted parameters and can execute automatic classification of the objective sediment components.

The classification results executed by the classification unit 79 are supplied to a central control unit 80. Then, a storage necessity judging unit 801 included in the central control unit 80 judges whether or not the classified components are to be stored in a form of images according to a predetermined condition and when judged it is necessary to store the images, the images are stored in an image storage unit 81. The central control unit 80 also performs such functions as signal transmission and reception with the image processing control unit 76, issues image display commands to a display 82 and receives command signals from a key board 83. Since there are diversified types of urine sediment components, it is sometimes impossible to classify all of the sediment components automatically and in some instances unclassifiable sediment components may appear. Therefore, the images of the unclassifiable urine sediment components are stored in the image storage unit 81.

Now, detection of passing particles in the flow cell 54 is explained.

A semiconductor laser 65 is always lighted, the light flux from the semiconductor laser 65 is converted into parallel light flux via a collimator lens 67, and a single direction of the light flux is focused via a cylindrical lens 68. The light flux from the cylindrical lens 68 is reflected via a reflection mirror 69 and a micro reflection mirror 64 and is focused at a laser focusing position on the sample 63 in the flow cell 54. Then, the laser beam is reflected via a beam splitter 70 and is supplied to a photo detector 72 via a stop 71. Signals from the photo detector 72 are supplied to a lighting control unit 73.

When sediment components of the measurement object pass through the laser beam in the flow cell 54, the laser beam is scattered. When a level of particle detection signal of the scattered light exceeds a predetermined level, the lighting control unit 73 judges that particles of image processing object are passing through a predetermined position, and when the particle reaches to another predetermined position in an image picking up region for the TV camera 58, the lighting control unit 73 controls a lamp drive circuit 77 so as to light the flash lamp 51.

The lighting period of the flash lamp 51 is set so short that the movement of a particle in the flow of the sample 63 is negligible. For this reason, when the flash lamp 51 is lighted, the video output signals of the TV camera 58 can pick up sediment components in the flow of sample 63 as still images.

Figure 10:
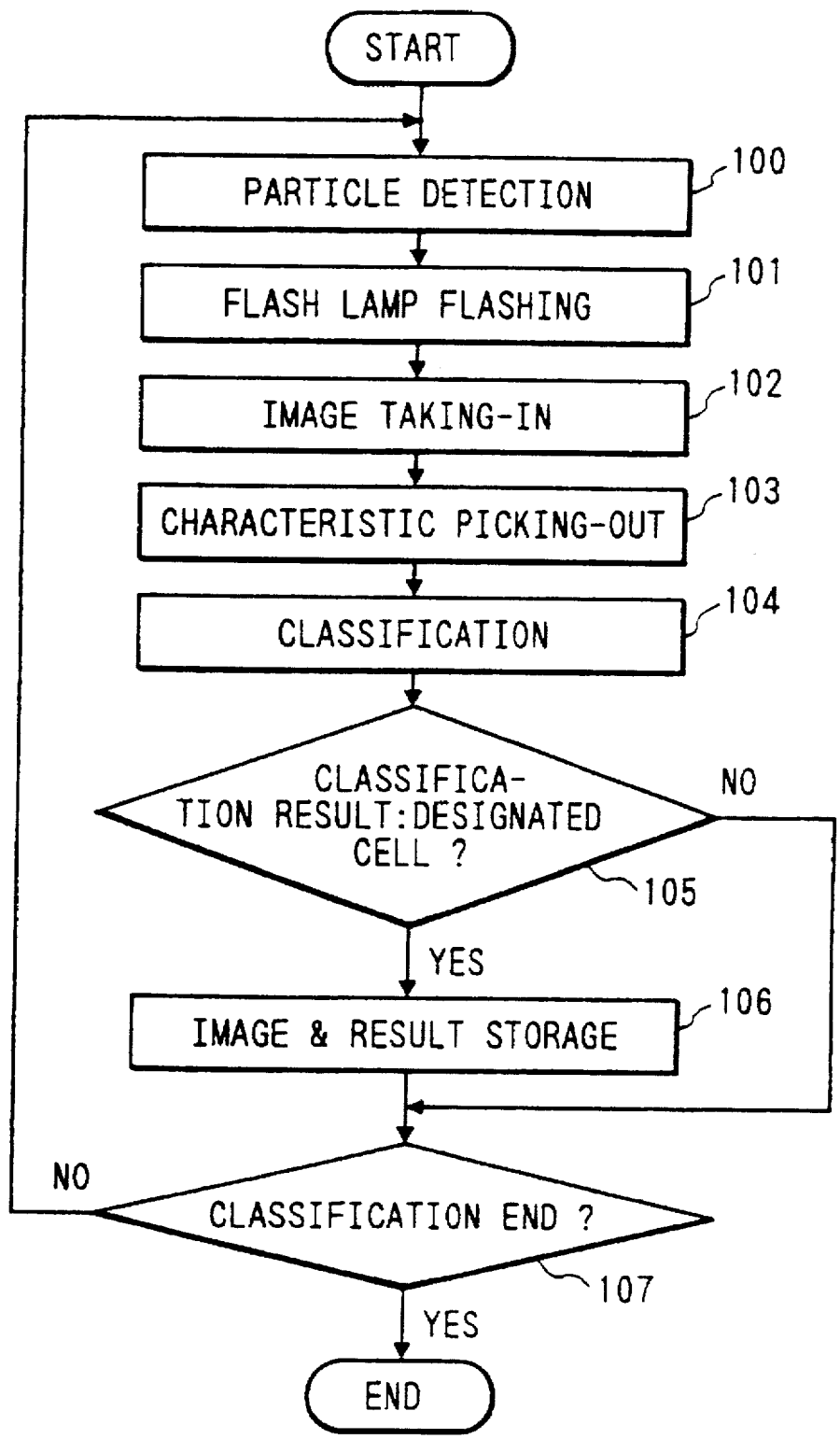
FIG. 10 is an operation flowchart in the embodiment as shown in FIG. 9.

FIG. 10 is a flowchart for explaining the operation of the embodiment as shown in FIG. 9.

In step 100 in FIG. 10, when a particle in the sample 63 is detected by the lighting control unit 73, the flash lamp 51 is lighted in step 101. Then, in step 102 an image is taken in via the TV camera 58, A/D converter 74 and image memory 75, and is supplied to the characteristic picking out unit 78. Thereafter, in step 103 the characteristic picking out unit 78 picks out characteristics of the particle from the taken in image.

Then, in step 104 the classification unit 79 classifies the particle. Subsequently, in step 105 the storage necessity judging unit 801 in the central control unit 80 judges whether the classification result corresponds to designated cells. When it is judged in step 105 that the classification result corresponds to one of the designated cells or is indiscernible, the process proceeds to step 106. In step 106, the central control unit 80 takes out the particle image stored in the image memory 75 via the image processing control unit 76 and the identification result and the particle image are stored in the image storage unit 81. In case when the particle is unidentifiable, the classification information determined in the classification unit 79 is stored together with the particle image in the image storage unit 81. Then the process proceeds to step 107. Further, when it is judged in step 105 that the classification result is discernible but does not correspond to one of the designated cells, the process also proceeds to step 107. Then, in step 107 completion of the classification is judged, and if not completed the process returns to step 100 and the steps 100 through 105 or steps 100 through 106 are repeated, but if completed the process ends. Further, the cell designation in step 105 is inputted beforehand into the central control unit 80 via the key board 83 by a user operator. Still further, when it is judged in step 105 that the classification result corresponds to a non-designated cell, the name of the cell can be displayed on the display 82.

Figure 11:
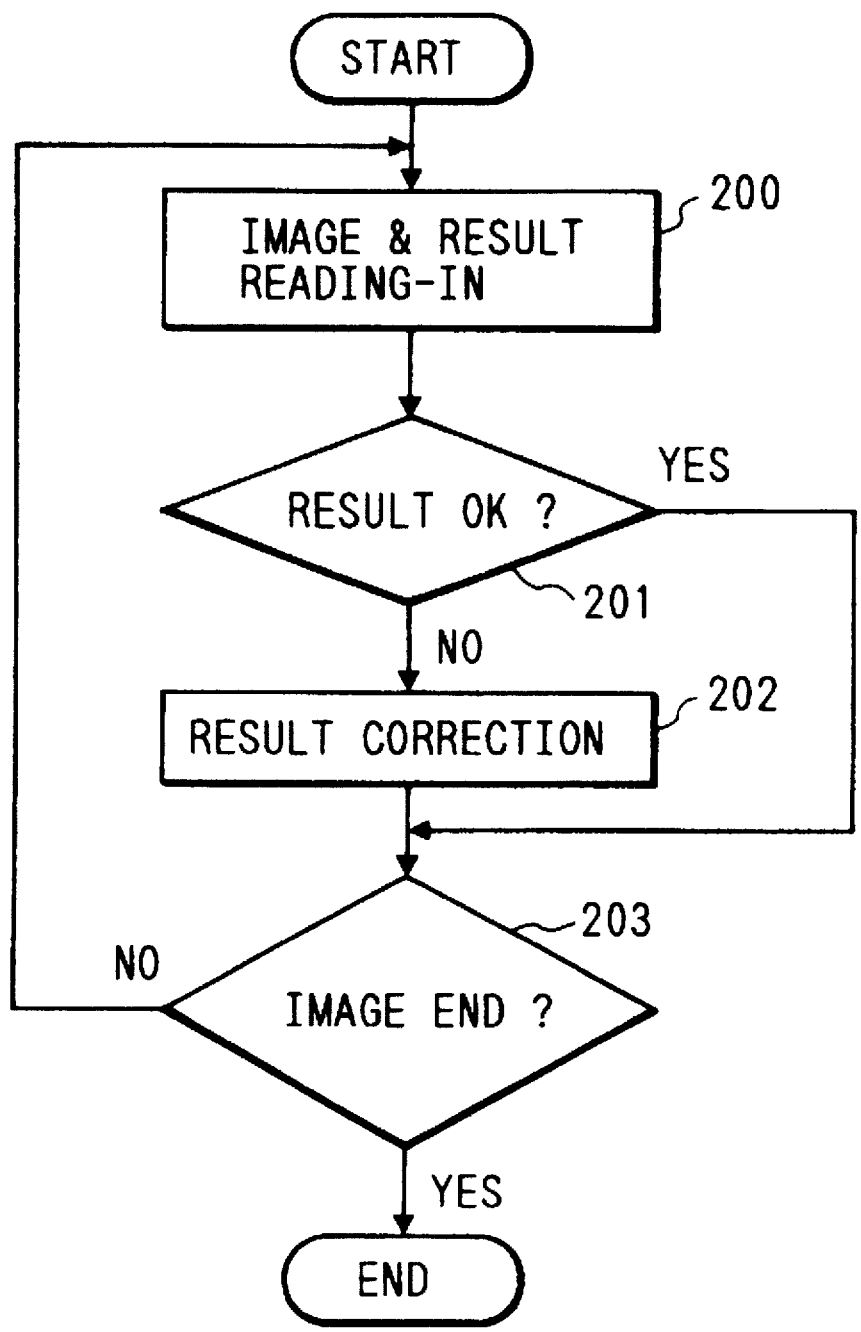
FIG. 11 is an operation flowchart in the embodiment as shown in FIG. 9 when stored images are read out.

FIG. 11 is a flowchart for in explaining the operation step 106 in FIG. 10 when for example, an examination engineer reviews and judges the stored images.

In step 200 in FIG. 11, the examination engineer commands to the central control unit 80 via the key board 83 to display the images stored in the image storage unit 81 on the display 82 during examination or any time after completing the examination. In response to the command, the central control unit 80 takes out determined results as well as the images of the sediment components from the image storage unit 81 and displays the same display image display 82. FIG. 12 shows an example of a displayed screen image. In the example of FIG. 12, eight flat epithelials among many detected particles are displayed and in addition detected numbers of such as leucocytes and erythrocytes are displayed. Two ordered ways of display can be selected, one according to classification category or item and the other according to appearing order of the particles in the flow cell. Subsequently, in step 201 the examination engineer reviews the determined results and the images displayed on the display 82 and judges whether the determined results are correct. When it is judged that the determined results are incorrect the process proceeds to step 202 and the results are corrected through manipulation of the key board 83 by the examination engineer. The classification unit 79 learns the newly determined results. Through this operation the classification capability of the classification unit 79 is improved. Then, the process proceeds to step 203. Further, when the determined results are judged correct in step 201, the process also proceeds to step 203. In step 203, it is judged whether the images to be read out are exhausted. If they are not exhausted the process returns to step 200 and repeats the steps 200 through 203, but if exhausted, the process ends.

In the present embodiment according to the present invention as explained above, the types of the detected particles in urine are comprehensively evaluated through a neural network in the classification unit 79. Further, with regard to indiscernible particles, their images and classification information are stored in the image storage unit 81, and the results determined as indiscernible are reviewed and corrected by a user such as an examination engineer. Then, the corrected information is supplied for learning to the classification unit 79. Accordingly, a urine particle classification and examination device, which allows accurate and fast automatic component particle analysis even for urine of non-healthy persons containing a variety of components in high concentration, can be realized. Further, the image storage unit 81 requires no large capacity, because the image storage unit 81 is designed to store only the images of indiscernible particles and predetermined ones such as designated cells.

FIG. 13 is a flowchart for explaining the operation of a further embodiment according to the present invention. Since the constitution of the device is substantially the same as that of the previous embodiment, the illustration thereof is omitted. However, in the present embodiment, the storage necessity judging unit 801 included in the central control unit 80 in the previous embodiment is excluded. Namely, the image storage method of the present embodiment is different from that of the previous embodiment. In the previous embodiment only the particle images of the designated components and indiscernible ones are stored; however, the present embodiment is designed to store images of all of the detected sediment components.

In FIG. 13, step 100 through step 104 are identical to those in FIG. 10. After executing the classification in step 104, the process proceeds to step 106 wherein the images of classified particles and the classification results are stored. Then the process proceeds to step 107 wherein the classification completion is judged, if not completed the process returns to step 100, and if completed the process ends.

Figure 14:
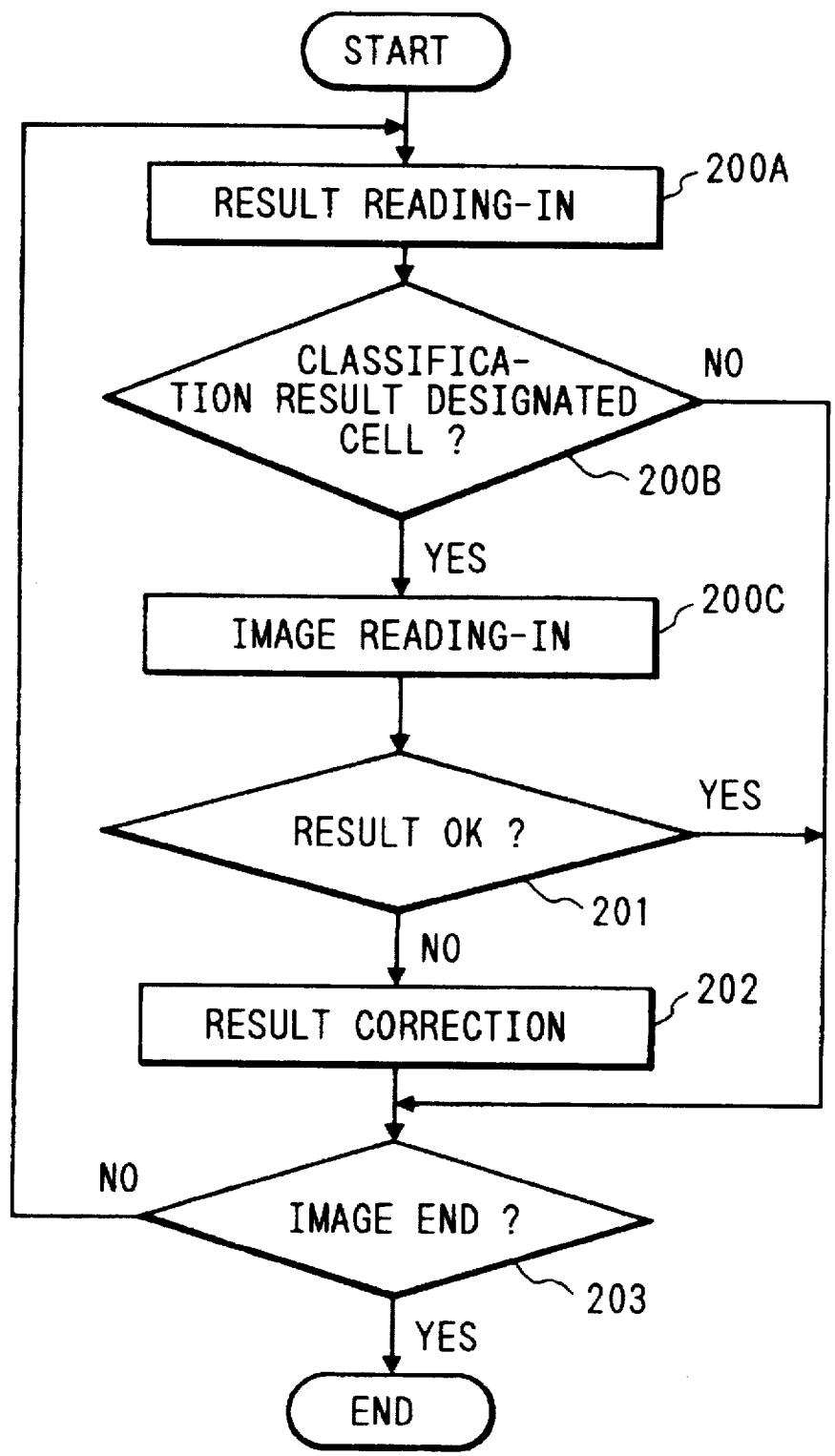
FIG. 14 is an operation flowchart in the second embodiment as shown in FIG. 13 when stored images are read out.

FIG. 14 is a flowchart for explaining the operations in step 106 in FIG. 13 when a user such as an examination engineer reviews and judges the images and classification results stored.

In step 200A in FIG. 14, the classification results stored are read in. Then, in step 200B it is judged whether the classification results correspond to the designated cells or are indiscernible ones. When the classification results neither correspond to the designated cells nor are indiscernible ones, the process proceeds to step 203. When it is determined in step 200B that the classification results either correspond to the designated cells or are indiscernible ones, the process proceeds to step 200C and the stored images are read in and displayed. Then it is judged in step 201 whether the classification results are correct, and if the results are correct, the process proceeds to step 203, but if the results are incorrect the process proceeds to step 202 wherein the results are corrected and the corrected information is transmitted to the classification unit 80 for learning. Thereafter, the process proceeds to step 203 wherein it is judged whether the images are exhausted, and if not exhausted, the process returns to step 200A and the steps 200A through 202 are repeated, but if exhausted the process ends.

Like the previous embodiment, with the present embodiment according to the present invention, a urine particle classification and examination device can be realized, which allows accurate and fast automatic component particle analysis even for urine of non-healthy persons containing a variety of components in high concentration.

Figure 15:
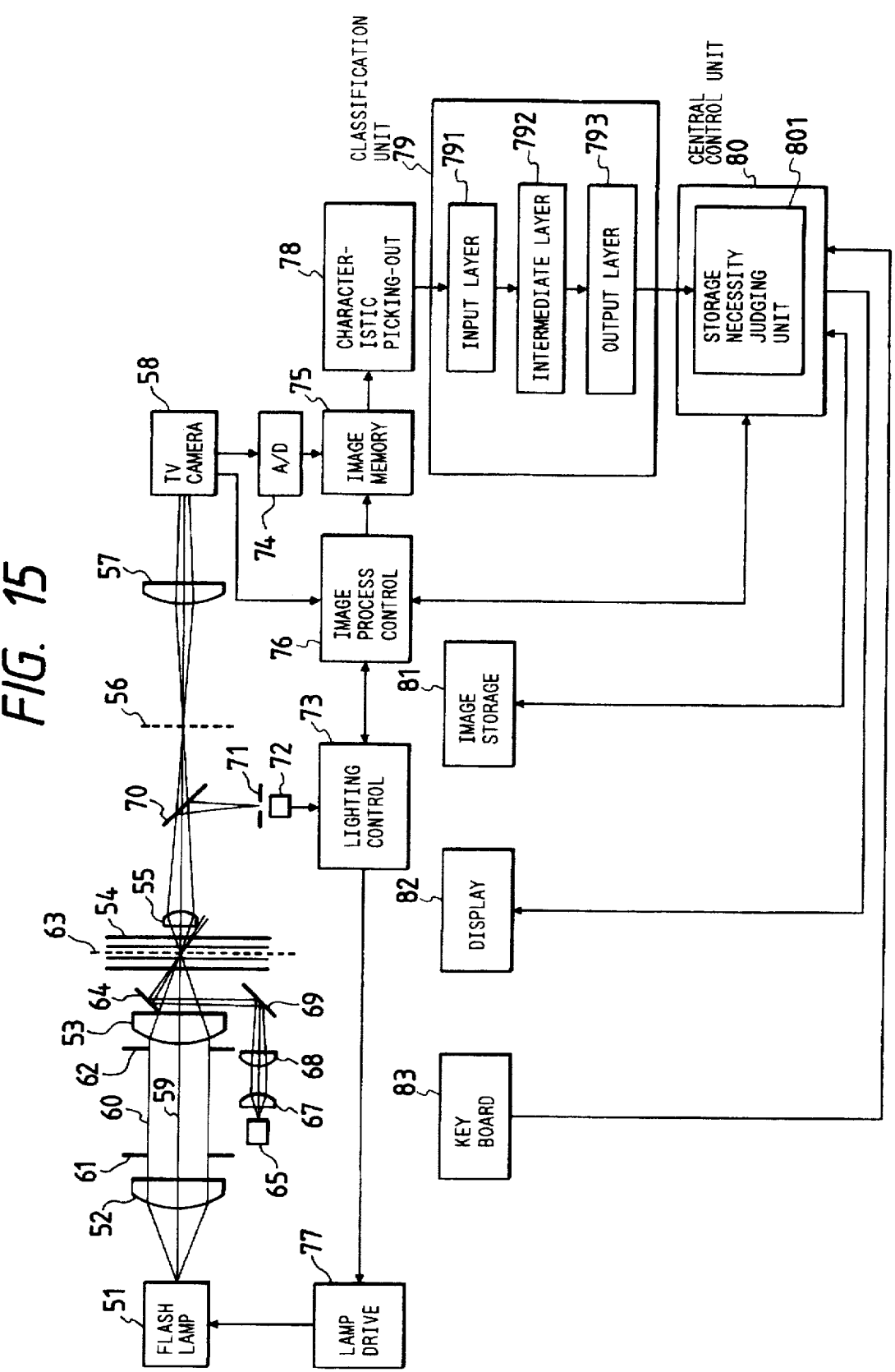
FIG. 15 is a schematic constitution diagram of a still further embodiment according to the present invention.

FIG. 15 is a schematic constitutional diagram of a still further embodiment according to the present invention. The constitutions of the present embodiment other than that of the classification unit 79 are substantially the same as those in the embodiment as shown in FIG. 9. Explanation of the same or equivalent portions thereof is omitted.

In FIG. 15, the classification unit 79 performs classification of particles by making use of a plurality of the characteristic quantities picked out by the characteristic picking out unit 78. The classification unit 79 forms a Rumelhart type neural network and is constituted by an input layer 791, an intermediate layer 792 and an output layer 793. The number of nodes at the input layer 791 corresponds to the number of characteristic quantities or parameters and the number of nodes at the output layer 793 corresponds to the number of types or classification items of the particles to be identified. The number of nodes at the intermediate layer 792 is determined so as to fulfill both requirements for calculation time and for identification accuracy.

Coupling coefficients between respective nodes in the neural network are optimized by making use of a great many characteristic quantities with certified results. Namely, the coupling coefficients for all of the characteristic quantities with certified results are determined in advance in such a manner that when characteristic quantities are inputted at the input layer 791 the output of a node at the output layer which corresponds to the identification result shows a maximum value.

When identifying an unknown particle, characteristic quantities thereof are input in the input layer 791, a neural network calculation is performed thereon and the node number of the output layer 793 providing the maximum value corresponds to the identification result. When the maximum value is over a predetermined slice level, the type corresponding to the outputting node number is determined as the identification result for the particle but when the maximum value is below the predetermined slice level, an identification failure is judged. In case of such an identification failure the classification unit 79 supplies a signal representing the identification failure to the central control unit 80. The central control unit 80 is provided with the storage necessity judging unit 801 and judges based on signals from the classification unit 79 whether the images are to be stored in the image storage unit 81.

As explained above, according to the present embodiment of the present invention, the types of the component particles detected in urine are comprehensively evaluated and identified via the neural network. Further, with regard to particles of identification failure, their images and classification information are stored in the image storage unit 81, the types of the particles are identified by a user such as an examination engineer and the identification result is inputted, such that by providing a correct result for the particle of identification failure into the neural network, the accuracy of the coupling coefficients between nodes can be further improved. Accordingly, like the embodiment in FIG. 9, a urine particle classification and examination device can be realized, which allows accurate and fast automatic component particle analysis even for urine of non-healthy persons containing a variety of components in high concentration. Further, the image storage unit 81 requires no large capacity, because the image storage unit 81 is designed to store only the images of indiscernible particles and predetermined ones such as designated cells.

Further, for the image storage unit 81 a magneto-optic disk having a large storage capacity and permitting erasing and rewriting can be used.

Still further, sediment components, for example heteromorphic cells and cancer cells of infrequent appearance but having a significant implication for clinical diagnosis can be stored in the image storage unit 81 depending on necessity.

Moreover, in the above embodiments the present invention is applied to a device for the classification and examination of particles in urine; however, the application of the present invention is not limited to the above embodiments and the present invention is likely applicable to a device for the classification and examination of particles in a variety of fluids.

Further, the following advantages are in addition obtained according to the present invention:

When someone such as an examination engineer performs a review of component particles through the display, the engineer can perform the review at any time, and a proper man-hour allocation in connection with the examination can be achieved.

Still further, when only the particle images whose types could not be identified are designed to be stored, the following advantages are further obtained:

(1) The storage capacity of the storage unit which stores images is reduced.

(2) The examination speed can be improved due to the reduction of the storage capacity of the image storage unit.

We claim:

1. A classification and examination device for classifying and examining particles in fluid, comprising:

an image pickup unit which picks up images of respective particles dispersed in a specimen flowing in a flow cell;

an image processing unit which analyzes the picked-up particle images, classifies the particles and displays the same;

wherein said image pickup unit picks up colored images of the respective particles;

said image processing unit converts each of the colored particle images into at least one binary image signal group based on a color standard, calculates a plurality of characteristic quantities of the respective particles based on the binary image signal group, automatically and provisionally classifies the type of the respective particles based on the characteristic quantities, and displays the colored particle images together with the automatic type classifications in a manner grouped according to the classified types; and means for permitting reclassification and learning based on the displayed colored particle images and the automatic type classifications thereof.

2. A classification and examination device according to claim 1, wherein said image processing unit comprises first means for storing both the colored particle images and the automatic type classifications thereof together with related data, with the specimen inputted by a user operator.

3. A classification and examination device according to claim 2, wherein the specimen is urine and the particles to be classified are sediments in the urine.

4. A classification and examination device according to claim 1, wherein said image processing unit comprises first means for arranging the colored particle images associated with the automatic type classifications according to a predetermined order of classification types at the same time.

5. A classification and examination device according to claim 4, wherein the specimen is urine and the particles to be classified are sediments in the urine.

6. A classification and examination device according to claim 1, wherein the means for permitting reclassification and learning permits the reclassification and the learning to be performed based on a neural network logic.

7. A classification and examination device according to claim 5, wherein the means for permitting reclassification and learning permits the reclassification and the learning to be performed manually.

8. A classification and examination device according to claim 6, wherein the specimen is urine and the particles to be classified are sediments in the urine.

9. A classification and examination device according to claim 1, wherein the means for permitting reclassification and learning permits manual reclassification and learning.

10. A classification and examination device according to claim 9, wherein the specimen is urine and the particles to be classified are sediments in the urine.

11. A classification and examination device according to claim 1, wherein the specimen is urine and the particles to be classified are sediments in the urine.

12. A classification and examination device for classifying and examining particles in fluid which by detecting the particles in fluid and picking up images of the detected particles, comprising:

a characteristic picking out unit which picks out a plurality of characteristics from the imaged particles;

a type identifying unit which automatically identifies the particles by type based on a plurality of the picked-out characteristics of the particles;

a storage unit which stores the picked-up particle images and the automatically identified types of the particles by said type identifying unit; and a display unit which selectively displays the images stored in said storage unit together with the automatically identified types thereof for permitting reclassification thereof by a user operator.

13. A classification and examination device according to claim 12, wherein said type identifying unit identifies types of the particles based on a neural network logic having a self learning capacity.

14. A classification and examination device for classifying and examining sediments in urine, comprising:

means for detecting sediment in urine flowing through a flow cell;

means for picking-up a colored still image of the sediment in response to the detection by said detecting means;

means for converting the picked-up colored still image of the sediment into at least one binary coded image signal group;

means for picking out a plurality of characteristic quantities of the binary coded image signal group of the sediment;

means for automatically classifying the detected sediment and for identifying the type of the detected sediment including identification failure based on a plurality of the picked-out characteristic quantities of the detected sediment, said automatic classification and identification means being constituted by a neurocomputer having a learning capability;

means for storing the image signal group of the sediment together with the automatic classification and identification result of the sediment determined in said automatic classification and identification means;

means for displaying the image of the sediment stored in said storage means in association with the automatic classification and identification result thereof for review by a user operator; and means for inputting a corrected type of the sediment determined by the user operator when the type of the sediment determined in said automatic classification and identification means is improper, for so informing the automatic classification and identification means for helping learning therein.

* * * * *